United States Patent
Voto et al.

(10) Patent No.: US 7,267,011 B2
(45) Date of Patent: Sep. 11, 2007

(54) DEVICE FOR INVASIVELY MEASURING FLUID PRESSURE

(75) Inventors: Andrew M. Voto, Brighton, MI (US); Ronald K. Selby, Flint, MI (US); Kenneth D. Perry, New Lothrop, MI (US); David A. Ross, Columbiaville, MI (US); Alfred V. Dumsa, Jr., Brighton, MI (US)

(73) Assignee: Delphi Technologies, Inc., Troy, MI (US)

( * ) Notice: Subject to any disclaimer, the term of this patent is extended or adjusted under 35 U.S.C. 154(b) by 12 days.

(21) Appl. No.: 11/242,208

(22) Filed: Oct. 3, 2005

(65) Prior Publication Data

US 2007/0074575 A1 Apr. 5, 2007

(51) Int. Cl.
*G01L 7/08* (2006.01)
(52) U.S. Cl. .......................... 73/715; 600/485
(58) Field of Classification Search ................ 600/485, 600/488, 494; 73/700, 730, 715
See application file for complete search history.

(56) References Cited

U.S. PATENT DOCUMENTS

| | | | |
|---|---|---|---|
| 3,818,765 A | 6/1974 | Eriksen | |
| 4,077,882 A | 3/1978 | Gangemi | |
| 4,226,124 A | 10/1980 | Kersten | |
| 4,554,927 A | 11/1985 | Fussell | |
| 5,105,820 A | 4/1992 | Moriuchi et al. | |
| 5,533,511 A * | 7/1996 | Kaspari et al. | 600/485 |
| 5,993,395 A * | 11/1999 | Shulze | 600/488 |
| 6,481,292 B1 | 11/2002 | Reich | |
| 6,695,789 B2 * | 2/2004 | Thede et al. | 600/494 |
| 2002/0198458 A1 | 12/2002 | Tripp, Jr. et al. | |
| 2003/0092999 A1 | 5/2003 | Goto et al. | |
| 2004/0059230 A1 * | 3/2004 | Thede et al. | 600/485 |

FOREIGN PATENT DOCUMENTS

GB 2 029 579 3/1980

\* cited by examiner

*Primary Examiner*—Andre J. Allen
(74) *Attorney, Agent, or Firm*—Scott A. McBain

(57) ABSTRACT

A device for invasively measuring fluid pressure is disclosed. The device includes a disposable housing having a fluid contacting area and a non-fluid contacting area. A disposable diaphragm in a substantially non-elastic state is disposed within the housing and separates the fluid contacting area from the non-fluid contacting area. A side of the diaphragm is adapted to contact the fluid, and the diaphragm has sufficient flexibility to move a distance axially within the non-fluid contacting area in response to fluid contact. The distance is substantially proportional to the fluid pressure. An electronic sensing device is removably attached adjacent the non-fluid contacting area of the housing, and is spaced from the diaphragm. The electronic sensing device is capable of determining the fluid pressure.

24 Claims, 2 Drawing Sheets

DEVICE FOR INVASIVELY MEASURING FLUID PRESSURE

BACKGROUND

The present disclosure relates generally to devices for measuring fluid pressure, and more particularly to devices for invasively measuring fluid pressure.

The monitoring of blood pressure in patients undergoing hemodialysis or infusion is usually performed with a non-disposable device. Such devices may include electronic sensors that have a saline buffer between the fluid and the sensor. One potential problem with non-disposable fluid pressure measuring devices is that the spread of disease may be substantially difficult to control. Various fluid-pressure devices use fluid (liquid or gel), generally contained between two diaphragms, as the media to transmit the pressure to the sensor that monitors pressure. One of the diaphragms conforms responsive to the pressure received, while the other contains the fluid.

Many diaphragms used in hemodialysis or infusion blood-pressure devices are in an elastic condition, which generally requires calibration between uses. These devices generally use both: well-controlled materials for the diaphragm and/or mounting of the diaphragm; and a calibration procedure that accounts for mounting and material variability. Such materials and calibration generally undesirably add to the expense of the device and efficiency of use thereof.

As such, it would be desirable to provide a device that is disposable, thereby substantially aiding in the prevention of bio-contamination from one patient to the next. Further, it would be desirable to provide such a device that generally does not require calibration between uses.

SUMMARY

A device for invasively measuring fluid pressure includes a disposable housing having a fluid contacting area and a non-fluid contacting area. A disposable diaphragm in a substantially non-elastic state is disposed within the housing and separates the fluid contacting area from the non-fluid contacting area. A side of the diaphragm is adapted to contact the fluid, and the diaphragm has sufficient flexibility to move a distance axially within the non-fluid contacting area in response to fluid contact. The distance is substantially proportional to the fluid pressure. An electronic sensing device is removably attached adjacent the non-fluid contacting area of the housing, and is spaced from the diaphragm. The electronic sensing device is capable of determining the fluid pressure.

BRIEF DESCRIPTION OF THE DRAWINGS

Objects, features and advantages of embodiments of the present disclosure will become apparent by reference to the following detailed description and drawings, in which like reference numerals correspond to similar, though not necessarily identical components. Reference numerals having a previously described function may not necessarily be described in connection with other drawings in which they appear.

DETAILED DESCRIPTION

Embodiment(s) of the device and method disclosed herein advantageously allow the invasive measuring of fluid pressure during procedures, such as, for example, hemodialysis or infusion, while substantially aiding in avoidance of bio-contamination of the sensor. A disposable housing as defined herein may substantially aid in maintaining the sterility of the device use, while allowing the more costly sensor and accompanying electronics to be reused.

Figure 1:
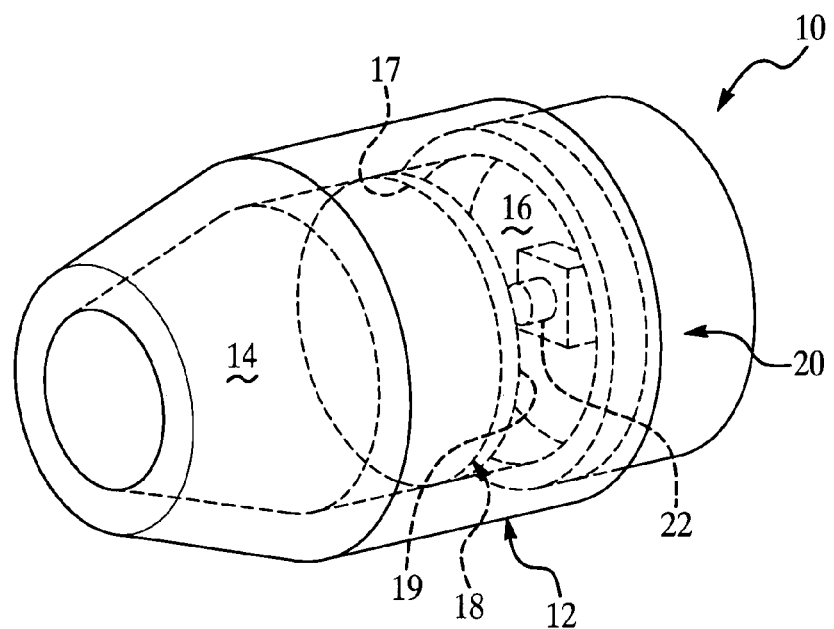
FIG. 1 is a semi-schematic perspective view of an embodiment of the invasive fluid pressure measuring device.

Referring now to FIG. 1, an embodiment of the device 10 for invasively measuring fluid (a non-limiting example of which is body fluid) pressure is depicted. The device 10 includes a disposable housing 12 having a fluid contacting area 14 and a non-fluid contacting area 16. It is to be understood that the housing 12 may have any suitable geometry, configuration, and/or may be molded with fittings for various applications. It is to be further understood that the device 10 may be utilized in any application that requires a method that substantially prevents contamination from one set of measurements to the next. This type of method is typical in many medical, biological, and/or chemical applications.

In an embodiment, the housing 12 generally has a substantially frusto-conical shape. Further, it is contemplated as being within the purview of the present disclosure that the housing 12 may be made of any suitable material, including, but not limited to metals (non-limitative examples of which include aluminum and stainless steel), engineering grade thermoplastics, and/or combinations thereof.

A disposable diaphragm 18 in a substantially non-elastic state/condition is operatively disposed within the housing 12. The diaphragm 18 is sealingly engaged within the housing 12 such that it separates the fluid contacting area 14 from the non-fluid contacting area 16. The diaphragm 18 is sealingly engaged with the housing 12 to substantially prevent fluid from entering the non-fluid contacting area 16. It is to be understood that embodiment(s) of the device 10 may still function if fluid enters the non-fluid contacting area 16, depending, at least in part, on the amount of fluid in the area 16, the type of fluid in the area 16, and the sensor used.

One side 17 of the diaphragm 18 is adapted to contact the fluid. It is to be understood that the diaphragm 18 has sufficient flexibility to move a distance axially within the non-fluid contacting area 16 in response to fluid contact with the fluid contacting side 17. In an embodiment, the axial distance moved by the diaphragm 18 is substantially proportional to the fluid pressure exerted on the fluid contacting side 17 of the diaphragm 18.

It is to be understood that the diaphragm 18 may be formed from any suitable material, depending at least in part upon the particular application in which the device 10 is desired for use. In a non-limitative example, the diaphragm 18 in a substantially non-elastic state is formed from various elastomeric materials.

The term "substantially non-elastic state/condition" as used herein refers to a sufficient flexibility of the diaphragm 18 that allows it to move in a predetermined direction, and substantially remain in that extended position, without being completely elastic. The diaphragm 18 may move without stretching its material fibers. The disposable diaphragm 18 in its non-elastic state substantially eliminates calibration steps (e.g. those that take into account the force needed to stretch an elastic material) generally required with a diaphragm in an elastic state. It is to be understood that the force used to move the diaphragm 18 in its non-elastic state remains substantially constant. Once a diaphragm enters its elastic state, an increase in force over a linear displacement may be required.

In an embodiment, the device 10 contains an electronic sensing device 22. The electronic sensing device 22 is operatively housed in a base 20 that is removably attached adjacent the non-fluid contacting area 16 of the housing 12. Sensing device 22 is spaced from the diaphragm 18. It is to be understood that the base 20, which contains the electronic sensing device 22, may be mounted directly in or on the medical device (not shown) being used; or base 20 may be an external mechanism that is electrically connected to the medical device through a wired or wireless connection.

In an embodiment, the base 20 is removeably attached to the housing 12 via any suitable means, including but not limited to snap fit, interference fit, threading engagement, quick connects, and/or combinations thereof. When the base 20 is attached to the housing 12, the non-fluid contacting area 16 is substantially sealed away from the ambient environment and the fluid. In this embodiment, the non-fluid contacting area 16 is sealed by a combination of the housing 12, a non-fluid contacting side 19 of the diaphragm 18, and the electronic sensing device 22.

Generally, the electronic sensing device 22 is capable of determining the pressure of the fluid that contacts the diaphragm 18. In an embodiment, the electronic sensing device 22 includes pressure sensors, such as silicon based piezo or microelectromechanical (MEMS) devices, or strain type measurement systems.

Figure 2:
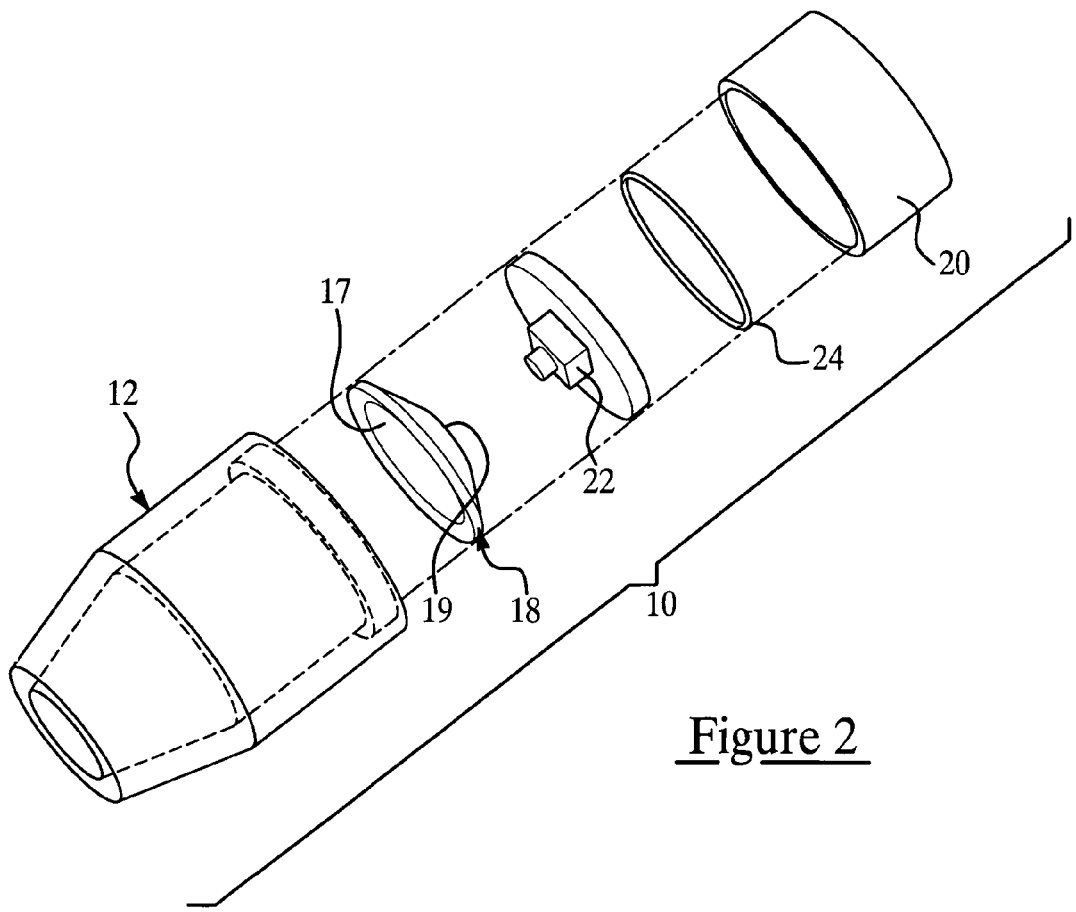
FIG. 2 is a semi-schematic, exploded perspective view of an embodiment of the invasive fluid pressure measuring device.

Referring now to FIG. 2, an exploded view of the device 10 shown in FIG. 1 is depicted. FIG. 2 depicts the following elements as described above: housing 12, diaphragm 18, base 20, and electronic sensing device 22. In addition, a sealing member 24 is shown. Sealing member 24 serves as a sealant between the housing 12 and the base 20. It is to be understood that seal member 24 may be formed from any suitable sealants. In an embodiment, seal member 24 includes at least one of O-rings, non-permeable die cut or molded gaskets, and/or combinations thereof.

Figure 3A:
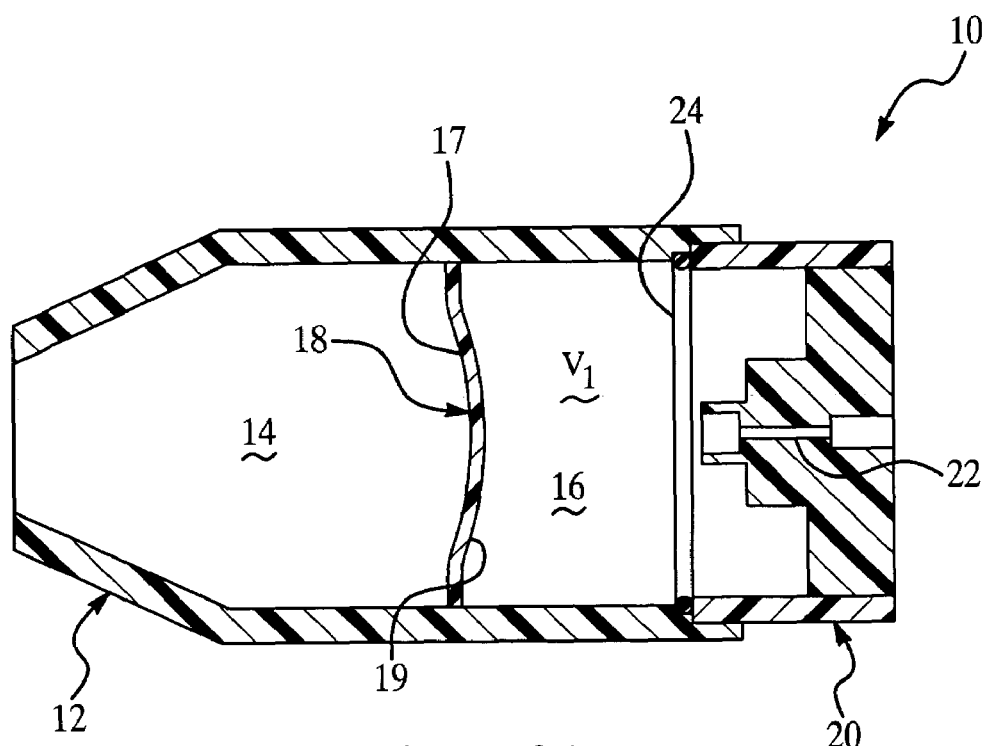
FIG. 3A is a cross-sectional, semi-schematic side view of an embodiment of the invasive fluid pressure measuring device prior to contacting fluid.
Figure 3B:
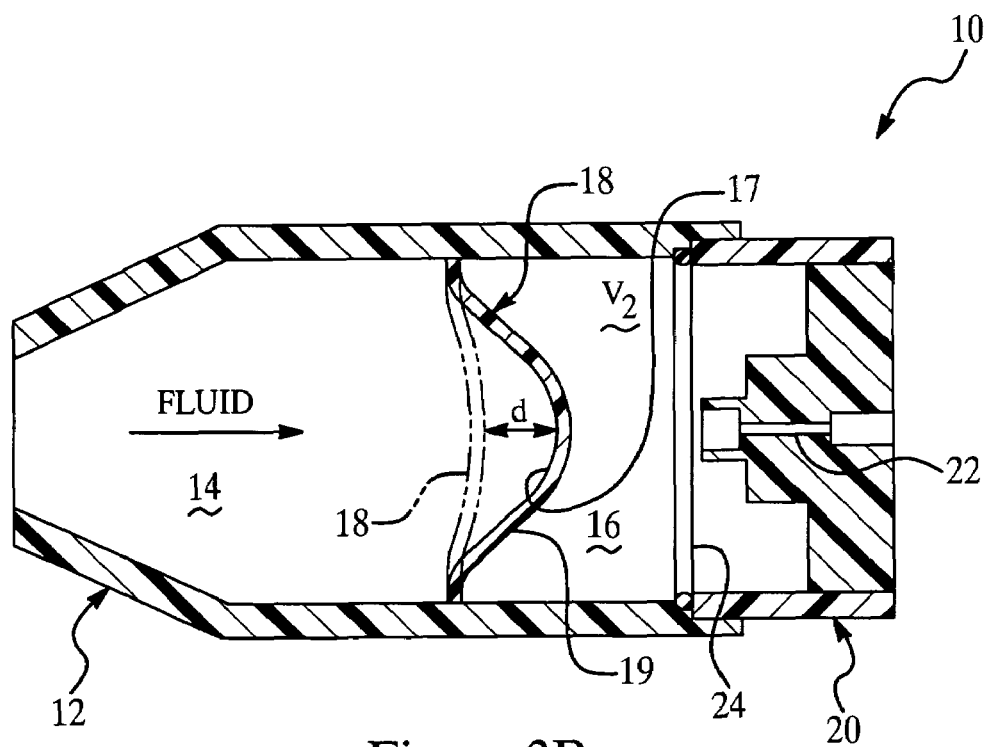
FIG. 3B is a view similar to that of FIG. 3A, but showing an embodiment of the invasive fluid pressure measuring device after contacting fluid.

Referring now to FIGS. 3A and 3B, the device 10 is shown in an embodiment of a pre-use (FIG. 3A) and use (FIG. 3B) state. In FIG. 3B, the housing 12 of the device 10 is placed in contact with the fluid (e.g. blood), the pressure of which is to be invasively measured. Fluid contacts at least a portion of the fluid contacting side 17 of the diaphragm 18, thereby moving the diaphragm 18 axially within the non-fluid contacting area 16 to equalize the pressure in the non-fluid contacting area 16. As the pressure is equalized, the electronic sensing device 22 is able to determine the fluid pressure without contacting the fluid.

FIG. 3A shows the diaphragm 18 in its non-expanded state before the introduction of fluid into the fluid-contacting area 14. Prior to fluid contact, the electronic sensing device 22 is capable of measuring an initial pressure, which is generally indicative of the ambient pressure. It is to be understood that the electronic sensing device 22 is also able to adjust itself to the then-prevailing ambient pressure prior to each use.

As shown in FIG. 3A, prior to fluid contact, the non-fluid contacting area 16 has an initial volume $V_1$. The electronic sensing system 22 measures the initial pressure in initial volume $V_1$, and later uses that measurement in determining the fluid pressure.

FIG. 3B depicts contacting at least a portion of the diaphragm 18 in its substantially non-elastic state with a fluid. The arrow indicates that fluid enters the fluid contacting area 14 of the housing 12 and then contacts the diaphragm 18. The fluid contacting area 14 may be designed with minimal or no volume, depending, at least in part on the application in which the device 10 is being used. A press and flow method provides movement of the diaphragm 18 and fills the volume of the fluid contacting area 14. Upon contact with the fluid, the diaphragm 18 moves axially a distance d within the non-fluid contacting area 14. The pre-use position of diaphragm 18 is shown in phantom.

It is to be understood that the distance d moved by the diaphragm 18 is substantially proportional to the pressure of the fluid that contacts diaphragm 18.

The non-fluid contacting area 16 contains air that is compressed when the diaphragm 18 expands in response to the fluid. As such, the initial volume $V_1$ of the non-fluid contacting area 16 changes as the diaphragm 18 moves. After the diaphragm is moved distance d to the use position, the non-fluid contacting area 16 has a final volume $V_2$. As depicted, the final volume $V_2$ is generally less than the initial volume $V_1$. As such, the volume of the non-contacting area 16 is substantially indirectly proportional to the fluid pressure.

The electronic sensing system 22 may be configured to determine the fluid pressure, which is a result of the change in volume (initial volume $V_1$ to final volume $V_2$) based on diaphragm 18 movement. It is to be understood that the initial pressure may be used as a reference pressure. In a non-limitative example, the fluid pressure may be determined by using the following formula:

$$V_2 = V_1 * P_1 / P_2$$

where $V_2$ is the final volume, $V_1$ is the initial volume, $P_1$ is the initial pressure, and $P_2$ is the final pressure. It is to be understood that the electronic sensing device 22 may be configured to calculate the final (i.e. fluid) pressure and then display the result to a user of the device 10.

In another embodiment, the electronic sensing system 22 may include a temperature sensor that takes an initial temperature reading in the non-fluid contacting area 16 and takes updated temperature readings as the diaphragm 18 moves. By monitoring the temperature, a change in temperature will not likely cause an unknown shift in the pressure. In a non-limitative example, the fluid pressure may be determined by using the following formula:

$$P_2 = P_1 * (T_2/T_1) * (V_1/V_2)$$

where $V_2$ is the final volume, $V_1$ is the initial volume, $P_1$ is the initial pressure, $P_2$ is the final pressure, $T_1$ is the initial temperature, and $T_2$ is the final temperature. The electronic sensing device 22 may be configured to calculate the final pressure and then display it to the user.

It is to be understood that embodiment(s) of the disposable housing 12 and diaphragm 18 may be discarded after one use, and that a new housing 12 and diaphragm 18 may be attached to the reusable base 20 (and sensing device 22) for the next use. This design substantially decreases the cost of the device 10, as the relatively costly electronic sensing device 22 is reusable. Further, the health care giver may not need to attach additional electrical connections, as they are provided in the base 20.

Upon removing the device 10 from the patient, the fluid in the device 10 may be drained so as to substantially prevent the fluid from dripping. In an embodiment where the electronic sensing device 22 is designed into a machine, the disposable portion of the device 10 may point downward so gravity assists in draining fluid from the device 10.

Embodiment(s) of the device 10 and method as disclosed herein include, but are not limited to the following advantages. The disposable housing 12 and diaphragm 18 may substantially aid in maintaining sterility of the device during use with multiple patients, as the fluid contacting portion of the device 10 is disposed of after one use. Further, the cost of the device 10 is substantially decreased, at least in part, because the electronic sensing device 22 may be reused. Yet further, the time interval between uses may generally be minimized, in that the housing 12 does not need to be sterilized between uses, nor does the device 10 need to be calibrated between uses to take into account the force necessary to move an elastic diaphragm (as opposed to the diaphragm 18 in a substantially non-elastic state as disclosed in embodiments herein).

While several embodiments have been described in detail, it will be apparent to those skilled in the art that the disclosed embodiments may be modified. Therefore, the foregoing description is to be considered exemplary rather than limiting.

What is claimed is:

1. A device for invasively measuring fluid pressure, the device comprising:
    a disposable housing having a fluid contacting area and a non-fluid contacting area;
    a disposable diaphragm in a substantially non-elastic state disposed within the housing and separating the fluid contacting area from the non-fluid contacting area, a side of the diaphragm adapted to contact the fluid, the diaphragm having sufficient flexibility to move a distance axially within the non-fluid contacting area in response to fluid contact, the distance being substantially proportional to the fluid pressure; and
    an electronic sensing device removably attached adjacent the non-fluid contacting area of the housing, and spaced from the diaphragm, the electronic sensing device capable of determining the fluid pressure.

2. The device as defined in claim 1 wherein the electronic sensing device is housed in a base that is removably attachable adjacent the non-fluid contacting area of the disposable housing.

3. The device as defined in claim 2 wherein the non-fluid contacting area is sealed when the base is attached to the disposable housing.

4. The device as defined in claim 1 wherein the base is removably attached to the disposable housing via a member selected from threads, snaps, quick connects, and combinations thereof.

5. The device as defined in claim 1 wherein the diaphragm comprises elastomeric materials.

6. The device as defined in claim 1 wherein the non-fluid contacting area has an initial volume prior to the fluid contacting the diaphragm and a final volume after the fluid contacts the diaphragm, wherein the initial volume is greater than the final volume.

7. The device as defined in claim 6 wherein the electronic sensing device is capable of determining the fluid pressure via a change in volume.

8. The device as defined in claim 7 wherein the pressure is substantially indirectly proportional to the volume.

9. The device as defined in claim 1 wherein the diaphragm is sealingly engaged with the disposable housing to substantially prevent fluid from entering the non-fluid contacting area.

10. The device as defined in claim 1 wherein the electronic sensing device includes a pressure sensor.

11. The device as defined in claim 10 wherein the electronic sensing device further includes a temperature sensor.

12. The device as defined in claim 1 wherein the fluid is a body fluid.

13. The device as defined in claim 1 wherein the electronic sensing device is electrically connected to a medical device.

14. The device as defined in claim 13 wherein the electronic sensing device is electrically connected to the medical device via one of a wired connection and a wireless connection.

15. The device as defined in claim 1 wherein the non-fluid contacting area contains air that is compressed when the disposable diaphragm expands in response to the fluid contact.

16. A method for invasively measuring fluid pressure, the method comprising:
    contacting a disposable diaphragm with a fluid, the diaphragm in a substantially non-elastic state and sealingly disposed within a disposable housing, the diaphragm separating a fluid-contacting area from a sealed non-fluid contacting area, the contacting axially moving the diaphragm a distance within the non-fluid contacting area in response to the fluid contact, the distance being substantially proportional to the fluid pressure; and
    determining the fluid pressure based on the diaphragm movement.

17. The method as defined in claim 16 wherein contacting the diaphragm with the fluid is accomplished during at least one of hemodialysis and infusion.

18. The method as defined in claim 16 wherein an electronic sensing system is configured to determine the fluid pressure.

19. The method as defined in claim 16 wherein the non-fluid contacting area contains air, and wherein the air is compressed when the diaphragm moves within the non-fluid contacting area.

20. The method as defined in claim 16 wherein the non-fluid contacting area is sealed by: the housing; a non-fluid contacting side of the diaphragm; and an electronic sensing device removably attached adjacent the non-fluid contacting area of the housing and spaced from the diaphragm.

21. A method for invasively measuring fluid pressure, the method comprising:
    providing a disposable housing having a disposable diaphragm in a substantially non-elastic state therein that separates a fluid contacting area from a non-fluid contacting area;
    exposing the fluid contacting area to a fluid, whereby at least some of the fluid contacts the diaphragm, thereby axially moving the diaphragm a distance within the non-fluid contacting area, the distance substantially proportional to the fluid pressure; and
    measuring a pressure of the non-fluid contacting area after the diaphragm moves the distance within the non-fluid contacting area.

22. The method as defined in claim 21 wherein the measuring is accomplished by an electronic sensing system including a pressure sensor and a temperature sensor.

23. The method as defined in claim 21 wherein the measuring is accomplished by an electronic sensing system including a pressure sensor.

24. The method as defined in claim 21 wherein air contained in the non-fluid contacting area compresses when the disposable diaphragm moves in response to the fluid contact.

* * * * *